United States Patent [19]

Betzing et al.

[11] 4,129,650

[45] Dec. 12, 1978

[54] NOVEL PHOSPHOLIPID DERIVATIVES OF PROSTAGLANDINS AND PROCESS OF THEIR PREPARATION

[75] Inventors: Hans Betzing, Horrem; Dac Lekim, Cologne, both of Germany

[73] Assignee: A. Nattermann & Cie. GmbH, Cologne, Germany

[21] Appl. No.: 810,820

[22] Filed: Jun. 28, 1977

[30] Foreign Application Priority Data

Jun. 29, 1976 [DE] Fed. Rep. of Germany ....... 2629135

[51] Int. Cl.² .................. A61K 31/66; A61K 31/685; C07F 9/02
[52] U.S. Cl. .................................. 424/211; 260/403; 424/199; 424/212
[58] Field of Search ................ 260/403; 424/199, 212, 424/211

[56] References Cited

U.S. PATENT DOCUMENTS

| 3,632,627 | 1/1972 | Gordon et al. | 260/403 |
| 3,746,728 | 7/1973 | Gordon et al. | 260/403 |

Primary Examiner—Sam Rosen
Attorney, Agent, or Firm—Karl W. Flocks

[57] ABSTRACT

A compound of the formula

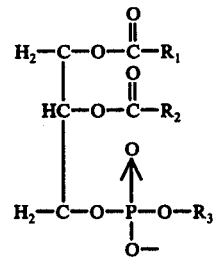

(wherein $R_1$ and $R_2$ are each H or a fatty-acid residue, and $R_3$ is

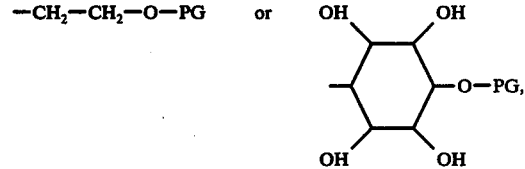

and PG is a prostaglandin radical or optical isomer thereof) is found to have a substantially increased duration of effect, compared with the corresponding prostaglandin per se, and also a strong organ specificity.

6 Claims, No Drawings

NOVEL PHOSPHOLIPID DERIVATIVES OF PROSTAGLANDINS AND PROCESS OF THEIR PREPARATION

BACKGROUND OF THE INVENTION

Prostaglandins are a group of long-chain, unsaturated hydroxy and hydroxyketocarboxylic acids comprising a cyclopentane ring. From the chemical point of view, prostaglandins are derivatives of prostan-acid, which has the following structure:

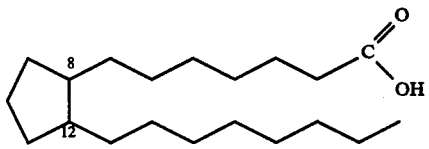

There exists a series of prostaglandins occuring in nature. The prostaglandin $PGE_1$, for example, has the following structure

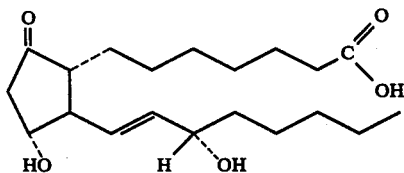

while prostaglandin $PGF_1$ corresponds to the following structure

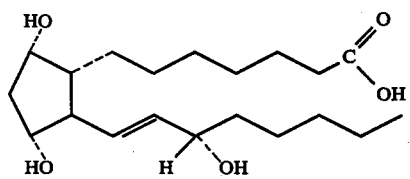

and prostaglandin $PGA_1$ corresponds to the following structure

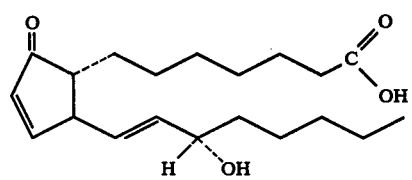

Prostaglandins occur in the tissue of many mammals in different quantitative ratios and a corresponding variety can be observed also in regard to the physiological properties of this class of compounds. There is known to be a series of quite important pharmacological effects associated with separate prostaglandins. In addition to influencing the heart frequency and lowering the blood pressure, prostaglandins also prevent the adhesion and aggregation of platelets, which represent the first step to thrombosis.

However, in spite of such quite valuable spectrum of effects, prostaglandins could hardly be used for pharmacological purposes until the present time, since their half-value life in blood amounts to only about 10 minutes. Accordingly, in the past there has been no lack of experiments in attempting to eliminate this deficiency through the provision of suitable derivatives of prostaglandin. Thus, the U.S. Pat. Nos. 3,632,627 and 3,746,728 describe processes of esterifying prostaglandins with glycerin or esters of glycerophosphoric acid, in which connection one obtains ester compounds corresponding to the formula

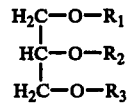

wherein one of the radicals $R_1$, $R_2$, $R_3$ is a prostaglandin group, the other radicals being, as the case may be, hydrogen or radicals of stearic acid, palmitic acid or phosphoric acid having the formula

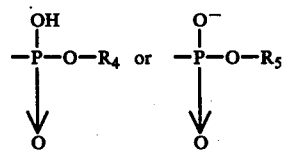

wherein $R_4$ is hydrogen or the

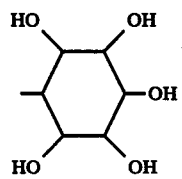

radical, while $R_5$ can be one of the groups:

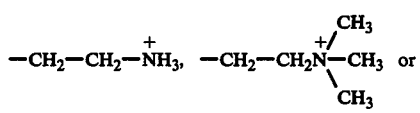

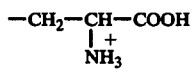

The physiological effectiveness of these compounds, i.e., the duration of effect of the prostaglandins, should be extended through the formation of derivatives.

SUMMARY OF THE INVENTION

It has now been found that ester or amide derivatives of the prostaglandins with phospholipids still possessing reactive groups in the molecule, such as phosphatidylethanolamine, phosphatidyl inositide, phosphatidyl serine and phosphatidyl glycol, possess not only a certain depot effect, i.e., a delayed release of the effective substance and a substantially increased duration of effect, but unexpectedly also a strong organ specificity concerning the effect observed.

For example, the prostaglandin $F_2$ derivative of phosphatidyl ethanolamine after i.v. administration thus exhibits practically no activity in the blood and only a low activity in the liver and the stomach; on the other hand, it exhibits a strong activity in the spleen and in the pancreas. Also the other prostaglandins in the form of the phospholipid compounds of the invention possess similar specific effectiveness, so that this new group of compounds leads to a valuable enrichment of the pharmacopoeia.

DETAILED DESCRIPTION OF EMBODIMENTS

The phospholipid prostaglandin derivatives of the invention correspond to the following general structure

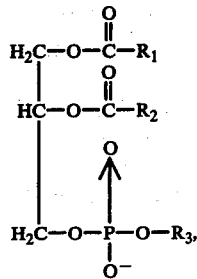

wherein $R_1$ and $R_2$ indicate hydrogen or a fatty-acid radical, e.g. where one of $R_1$ or $R_2$ is hydrogen and the other is a fatty-acid radical or where both are fatty-acid radicals, such as a radical of palmitic acid, stearic acid, oleic acid, linoleic acid, linolenic acid or arachidonic acid, while $R_3$ can be one of the following groups:

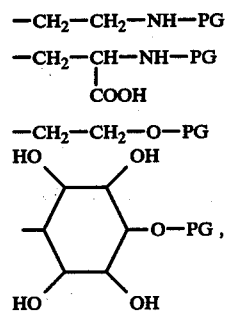

where PG represents a prostaglandin radical, such as $PGE_1$, $PGE_2$, $PGE_3$, $PGF_1$, $PGF_2$, $PGA_1$, $PGB_1$ or their optical isomers.

The prostaglandins needed for the new derivatives can be prepared fully synthetically or biochemically in accordance with processes known from the literature. For transformation into the phospholipid derivatives of the invention, the prostaglandins can be reacted in accordance with the invention so as to produce amides or esters with the corresponding phospholipids in a suitable solvent. The phosphatides are dissolved for this purpose in an inert solvent and the reaction is allowed to run in connection with the addition of dicyclohexylcarbodiimide, under the protection of an inert gas, preferably at temperatures lower than 50° C.

As inert organic solvents for the purpose of the invention, one can use, e.g., chlorinated hydrocarbons (such as carbon tetrachloride, chloroform, dichloroethane, etc.) pyridine, aliphatic, aromatic as well as cyclic hydrocarbons.

The reaction is generally completed within 48 hours. The product of the reaction can be purified through generally customary methods, but preferably through column-type chromatography on silica or silicic acid, or through preparative thin-layer chromatography.

The following specific working examples are offerred illustratively:

EXAMPLE 1

N-11α,15α-dihydroxy-9-keto-5,13-prostadienyl-phosphatidyl ethanolamine

Phosphatidyl ethanolamine was purified from crude soy phosphatide through column-type chromatography and 15α,15α-dihydroxy-9-keto-5,13-prostadienoic acid ($PGE_2$) was prepared biochemically.

250 mg (about 0.33 mmol) of phosphatidyl ethanolamine was dissolved in 20 ml dry chloroform. 100 mg $PGE_2$ (0.28 mmol), dissolved in 20 ml dry chloroform was added and then 64 mg (0.31 mmol) dicyclohexylcarbodiimide in 10 ml chloroform was also added. The reactive mixture was stirred overnight at room temperature. It was concentrated in vacuo. The product was obtained in the form of a yellow oil through column-type chromatography with silica and chloroform/methanol as eluent.

The yield amounted to 206 mg (0.21 mmol) or 75% of the theory. The infrared spectrum (KBr-briquette) showed the main absorption at 3450, 3050, 2925, 2860, 1740 and 1650 cm$^{-1}$.

The following was obtained in the same manner:

$PGE_1$ derivative of
N-11α,15α-dihydroxy-9-keto-13-prostenylphosphatidyl ethanolamine

EXAMPLE 2

1,2-diacyl-sn-nglycerto-3-phospho-(9,11,15-trihydroxy-13-prostenyl)-glycol 9,11,15-trihydroxy-13-prostenoic acid ($PGF_1$) was synthesized in accordance with the process given in the literature (E. J. Corey et al (1970) J. Am. Oil Chem. Soc. 92, 397 and 2586). Phosphatidyl glycol was prepared in accordance with the German Pat. No. 1,949,399 from phosphatidyl ethanolamine and purified through column-type chromatography.

115 mg $PGF_1$ (0.3 mmol) was dissolved in 5 ml dry pyridine and mixed with 300 mg trichlorethoxycarbonyl chloride in 5 ml dry pyridine. The reactive mixture was stirred overnight at room temperature, concentrated in vacuo and purified through silica (silicic-acid) column-type chromatography.

The obtained 9,11,15-tris-trichlorethoxycarbonyloxy-13-prostenoic acid was dissolved in 10 ml dry pyridine and mixed with 375 mg (about 0.5 mmol) phosphatidyl glycol and 125 mg (0.6 mmol) dicyclohexylcarbodiimide in 10 ml dry pyridine. The reactive mixture was stirred overnight, then concentrated in vacuo and freed of the protective group with zinc and glacial acetic acid. The product was obtained as a yellow oil by means of silica column-type chromatography. IR: 3450, 3050, 2920, 2850 and 1740 cm$^{-1}$.

In the same manner one obtained the $PGF_2$ derivative of the phosphatidyl inositide 1,2-diacyl-sn-glycero-3-phospho-(9,11,15-dihydroxy-5,13-prostadienyl)-isonite in the form of yellow oil.

It is to be understood that the invention is not limited to the embodiments disclosed above which are illustratively offered, and that modifications may be made without departing from the scope of the invention.

What is claimed is:

1. An ester or amide derivative of natural prostaglandin and having the formula

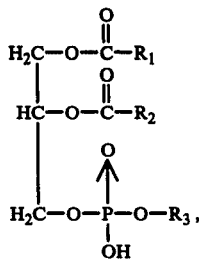

wherein $R_1$ and $R_2$ are each hydrogen or a fatty-acid radical with the proviso that at least one of $R_1$ or $R_2$ is a fatty-acid radical, and $R_3$ is one of the following groups

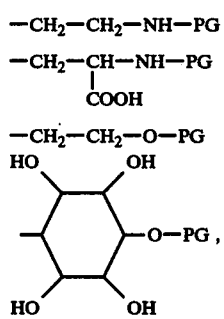

wherein PG is a prostagladin radical or its optical isomer, said PG being attached to the phospholipid through the carboxyl moiety.

2. A process of preparing a compound of claim 1, wherein the phospholipid is reacted with a prostaglandin in the presence of dicyclohexylcarbodiimide.

3. A process as in claim 2, wherein said prostaglandin is protected by a protective group, which is split off under mild conditions after the reaction is completed.

4. A medicament composition comprising a pharmaceutical excipient and a compound of claim 1 in an amount sufficient to lower blood pressure.

5. A compound in accordance with claim 1 of the formula

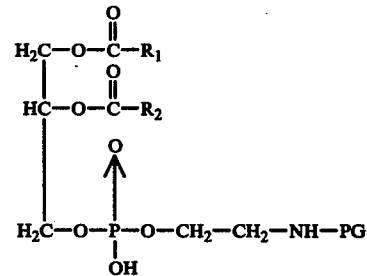

6. A compound in accordance with claim 1 wherein $R_1$ and $R_2$ are both fatty acids.

* * * * *